(12) United States Patent
Bailey et al.

(10) Patent No.: US 6,617,360 B1
(45) Date of Patent: Sep. 9, 2003

(54) MEDICAL TREATMENT

(75) Inventors: Clifford James Bailey, Birmingham (GB); Robert Brian Jones, Nottingham (GB); Helen Christine Jackson, Nottingham (GB)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/702,125

(22) Filed: Oct. 30, 2000

Related U.S. Application Data

(62) Division of application No. 09/254,924, filed as application No. PCT/EP97/05039 on Sep. 15, 1997, now Pat. No. 6,174,925.

(30) Foreign Application Priority Data

Sep. 21, 1996 (GB) .............................................. 9619757

(51) Int. Cl.$^7$ .................... A61K 31/135; A61K 31/255; A61K 31/155
(52) U.S. Cl. ......................... 514/646; 514/518; 514/635
(58) Field of Search ................................ 514/646, 635, 514/518

(56) References Cited

U.S. PATENT DOCUMENTS

| | | | |
|---|---|---|---|
| 4,939,175 A | | 7/1990 | Ukai et al. .................... 514/646 |
| 5,459,164 A | * | 10/1995 | Vargas .......................... 514/646 |
| 6,174,925 B1 | * | 1/2001 | Bailey et al. ................. 514/646 |

FOREIGN PATENT DOCUMENTS

| | | |
|---|---|---|
| EP | 230 742 | 8/1987 |
| EP | 282 206 | 9/1988 |
| EP | 397 831 | 11/1990 |
| GB | 2098602 | 11/1982 |
| WO | 90/06110 | 6/1990 |
| WO | 95/20949 | 2/1994 |
| WO | 95/10292 | 4/1995 |

OTHER PUBLICATIONS

Budavari et al., The Merck Index, Twelfth Edition (1996), pp. 754 and 1014, abstract Nos. 4448 and 6001.*

Bailey, CJ et al., "Influence of Genetic Background and Age on the Expression of the Obese Hyperglycaemic Syndrome in Aston ob/ob Mice", International Journal of Obesity, 6,11–21, 1982.

Flatt, PR, et al., "Development of Glucose Intolerance and Impaired Plasma Insulin Response to Glucose in Obese Hyperglycaemic (ob/ob) Mice", Horm. Metab. Res 13, 556–560, 1981.

Jones RB et al., "Chronic Administration of Sibutramine Reduces Plasma Glucose Levels in Obese Hyperglycaemic (ob/ob) Mice", Br J Pharmacol, vol. 120, 352, 1997.

Klip, A et al., "Stimulation of Hexose Transport by Metformin in L6 Muscle Cells in Culture", Endocrinolgy, vol. 130, No 5, 2535–2544 1992.

Lean MEJ. "Sibutramine –a Review of Clinical Efficacy", International Journal of Obesity, 21, S30–S36, 1997.

Laurence, DR, et al., Clinical Pharmacology, Seventh Edition, 577–578, 1992.

Vargas, R et al., "Effects of Sibutramine (S) vs. Placebo (P) in Niddm", Clinical Pharmacology and Therapeutics, Feb. 1994.

Walker, PS, et al., "Glucose Transport Activity in L6 Muscle Cells Is Regulated by the Coordinate Control of Subcellular Glucose Transporter Diswtribution, Biosynthesis, and mRNA Transcription", The Journal of Biological Chemistry, vol. 265, No. 3, 1516–1523, 1990.

* cited by examiner

Primary Examiner—Kevin E. Weddington
(74) Attorney, Agent, or Firm—John D. Conway; Tara Seshadri

(57) ABSTRACT

A compound of formula I

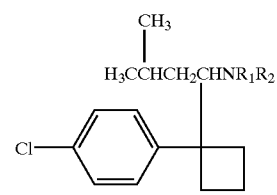

or a pharmaceutically acceptable salt thereof in which $R_1$ and $R_2$ are independently H or methyl (for example N,N-dimethyl-1-[1-(4-chlorophenyl)cyclobutyl]-3-methylbutyl amine hydrochloride optionally in the form of its monohydrate) is used for reducing Insulin resistance in humans in whom Impaired Glucose Tolerance and Non-Insulin Dependent Diabetes Mellitus have not presented.

14 Claims, 3 Drawing Sheets

MEDICAL TREATMENT

Figure 1:
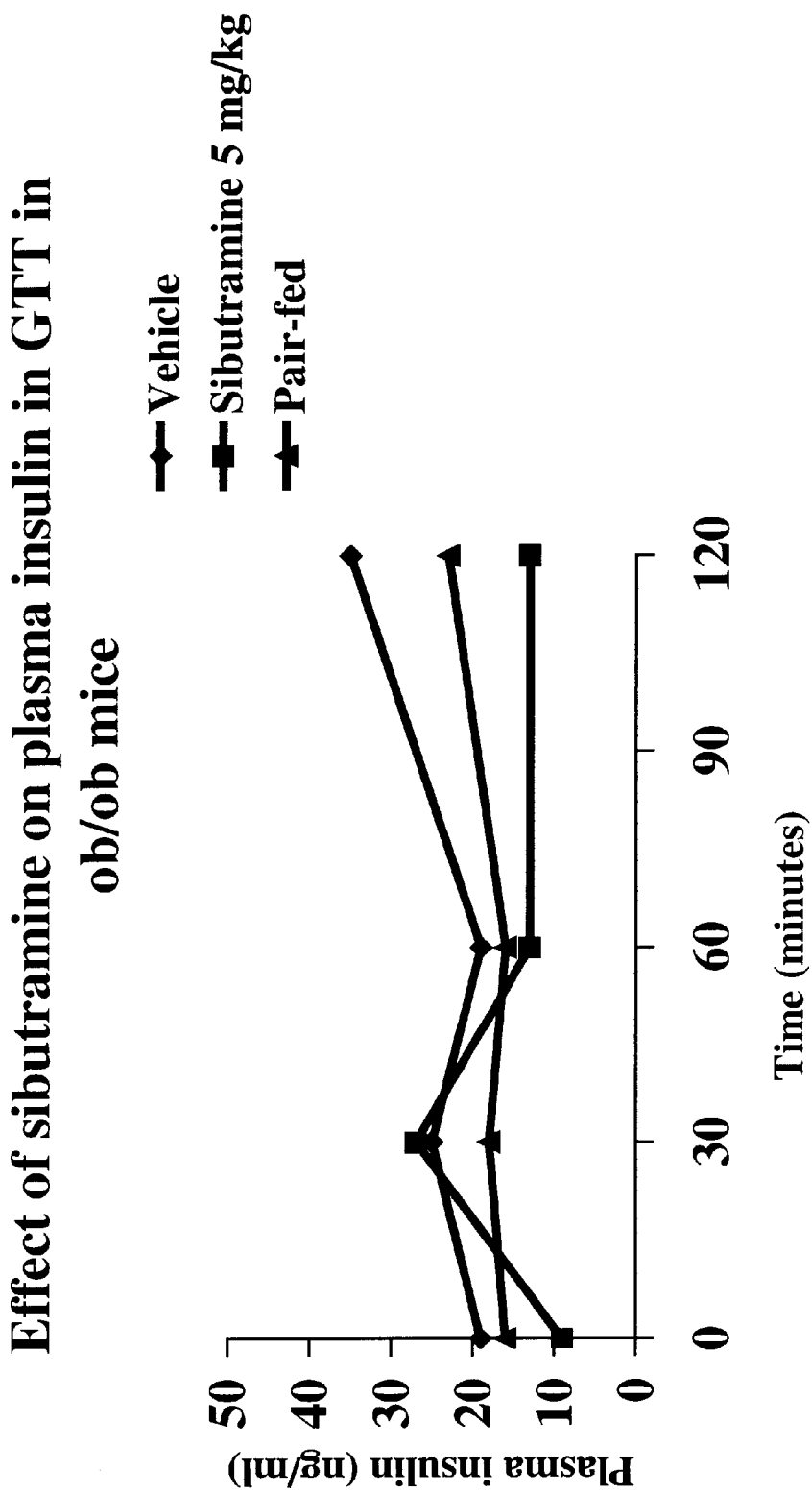

This is a divisional application of Ser. No. 09/254,924, which was filed as PCT/EP/97/05039 on Sep. 15, 1997 now U.S. Pat. No. 6,174,925.

This invention relates to a method of reducing insulin resistance in humans in whom Impaired Glucose Tolerance (IGT) and Non-Insulin Dependent Diabetes Mellitus (NIDDM) have not presented.

At present, a person who has a fasting plasma glucose level of greater than 7.8 mmol/l is classified as being diabetic (although this value is currently under review and may soon be set at a lower level, between 6 and 7 mmol/l). However, there is a standard means of classifying whether or not a person is diabetic, and this is important when a person has a fasting blood glucose level just below the above stated level. This means is called the Oral Glucose Tolerance Test (OGTT).

The OGTT is conducted in the following manner. After an overnight fast of 10–16 hours, a fasting blood glucose reading is taken. Glucose (75 g) is administered orally in water (250–300 ml). A further blood glucose reading is taken after 2 hours. Diabetes is diagnosed if the fasting glucose level is greater than 7.8 mmol/l or if the 2 hour level is greater than 11.1 mmol/l. Impaired Glucose Tolerance (IGT) is diagnosed if the fasting glucose level is less than 7.8 mmol/l and the 2 hour value is in the range 7.8–11.1 mmol/l. Normal glucose tolerance is declared if both the fasting glucose level and the 2 hour level are less than 7.8 mmol/l.

The majority of people are non-diabetic and have normal glucose tolerance. A proportion of these people will be at risk of developing Impaired Glucose Tolerance and/or diabetes in the future. One well-documented risk-factor is obesity, in which mild insulin resistance is a common phenomenon. This is often compensated for in the obese body by an increase in the plasma insulin level. However, the body can only increase its insulin secretion to a certain level, so if the insulin resistance continues to worsen in an obese person, eventually the body will not be able to compensate by providing extra insulin. At this time the plasma glucose levels will start to become elevated, presenting IGT or Non-Insulin Dependent Diabetes Mellitus (NIDDM).

Clearly, this gradual decline towards IGT and NIDDM is undesirable both for the individual and in terms of the cost of healthcare. It would, therefore, be advantageous to restrict insulin resistance for as long as possible in these people.

The term "glucose tolerance" includes glucose disposal in muscle tissue, and hepatic glucose output.

The term "Insulin resistance" means a reduced biological response to insulin. Insulin resistance can involve effects on both hepatic glucose output and peripheral glucose uptake, and may be due to reduced insulin receptor numbers, reduced tyrosine kinase activity of the insulin receptor and/or abnormalities distal to the receptor.

Surprisingly, it has now been found that the administration of certain arylcyclobutylalkylamines has efficacy in reducing insulin resistance.

According to the present invention there is provided a method for reducing insulin resistance in humans in whom Impaired Glucose Tolerance or Non-Insulin Dependent Diabetes Mellitus have not presented but in whom there is an increased risk of developing such conditions, said method comprising administering to a human in need thereof a therapeutically effective amount of a compound of formula I

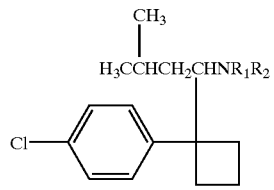

including enantiomers and pharmaceutically acceptable salts thereof, in which $R_1$ and $R_2$ are independently H or methyl, in conjunction with a pharmaceutically acceptable diluent or carrier. The human may be obese or may be not obese.

The preparation and use of compounds of formula I, such as N,N-dimethyl-1-[1-(4-chlorophenyl)cyclobutyl]-3-methylbutylamine (or N-{1-[1-(4-chlorophenyl)-cyclobutyl]-3-methylbutyl}-N,N-dimethylamine) and salts thereof. In the treatment of depression is described in British Patent Specification 2098602. The use of compounds of formula I such as N,N-dimethyl-1-[1-(4-chlorophenyl) cyclobutyl]-3-methylbutylamine and salts thereof in the treatment of Parkinson's disease is described in European Patent Number 282206. The use of N,N-dimethyl-1-[1-(4-chlorophenyl)cyclobutyl]-3-methylbutylamine and salts thereof in the treatment of cerebral function disorders is described in U.S. Pat. No. 4,939,175. The use of N,N-dimethyl-1-[1-(4-chlorophenyl)cyclobutyl]-3-methylbutylamine hydrochloride in the treatment of obesity is described in European Patent Number 397831. A particularly preferred form of this compound is N,N-dimethyl-1-[1-(4-chlorophenyl)cyclobutyl]-3-methylbutylamine hydrochloride monohydrate (sibutramine hydrochloride monohydrate) which is described in European Patent Number 230742. The use of N,N-dimethyl-1-[1-(4-chlorophenyl) cyclobutyl]-3-methylbutylamine and salts thereof for improving the glucose tolerance of humans having Impaired Glucose Tolerance or Non-Insulin Dependent Diabetes Mellitus is described in published PCT application WO95/20949. It does not disclose or suggest that the compounds of the present invention possess an insulin sensitising activity, nor does it disclose or suggest that the compounds of the present invention would be able to reduce insulin resistance in humans in whom IGT and NIDDM have not presented.

It may be appreciated by those skilled in the art that compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

It will be appreciated by those skilled in the art that compounds of formula I contain a chiral centre. When a compound of formula I contains a single chiral centre may exist in two enantiomeric forms. The present invention includes the use of the individual enantiomers and mixtures of the enantiomers. The enantiomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer to the other by asymmetric transformation.

Specific compounds of formula I are N,N-dimethyl-1-[1-(4-chlorophenyl)-cyclobutyl]-3-methylbutylamine, N-{1-[1-(4-chlorophenyl)cyclobutyl]-3-methylbutyl}-N-methylamine, and 1-[1-(4-chlorophenyl)cyclobutyl]-3-methylbutylamine including racemates, individual enantiomers and mixtures thereof, and pharmaceutically acceptable salts thereof. A preferred compound of formula I is N,N-dimethyl-1-[1-(4-chlorophenyl)-cyclobutyl]-3-methylbutylamine or a salt thereof, for example the hydrochloride salt. A preferred form of this hydrochloride is its monohydrate.

The compound of formula I may be administered in any of the known pharmaceutical dosage forms. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range 0.1 to 50 mg preferably 1 to 30 mg per day given in one or more doses.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compound with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 50 mg of the active compound.

Other dosage, forms for oral administration include, for example, aqueous suspensions containing the active compound in an aqueous medium in the presence of a non-toxic suspending agent such as sodium carboxy-methylcellulose, and oily suspensions containing a compound of the present invention in a suitable vegetable oil, for example arachis oil. The active compound may be formulated into granules with or without additional excipients. The granules may be ingested directly by the patent or they may be added to a suitable liquid carrier (for example, water) before ingestion. The granules may contain disintegrants, eg an effervescent couple formed from an acid and a carbonate or bicarbonate salt to facilitate dispersion in the liquid medium.

The therapeutically active compounds of formula I may be formulated into a composition which the patent retains in his mouth so that the active compound is administered through the mucosa of the mouth.

Dosage forms suitable for rectal administration are the known pharmaceutical forms for such administration, for example, suppositories with cocoa butter or polyethylene glycol bases.

Dosage forms suitable for parenteral administration are the known pharmaceutical forms for such administration, for example sterile suspensions or sterile solutions in a suitable solvent.

Dosage forms for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The therapeutically active compound of formula I may be formulated into a composition which is dispersed as an aerosol into the patients oral or nasal cavity. Such aerosols may be administered from a pump pack or from a pressurised pack containing a volatile propellant.

The therapeutically active compounds of formula I used in the method of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as an oily suspension of the compound to be infused for example in the form of a very sparingly water-soluble derivative such as a dodecanoate salt or a lipophilic ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The following in vitro and in vitro tests support the finding that compounds of formula I have efficacy in reducing insulin resistance, and may have an insulin sensitising action. It will be appreciated by those skilled in the art that 10 mg of sibutramine in the form of the hydrochloride monohydrate is equivalent to 8.37 mg of sibutramine as free base.

Study 1 In vitro L6 Muscle Cells

L6 Muscle cells were obtained from the European Culture Collection (Porton Down) and were used at passages 7–11. Cells were maintained in standard tissue culture medium DMEM, and glucose uptake was assessed using [$^3$H]-2-deoxyglucose (2DG) with and without the presence of added insulin ($10^{-8}$ M) as has been previously described (Walker P S et al, Glucose transport activity in L6 muscle cells is regulated by the coordinate control of subcellular glucose transporter distribution, biosynthesis, and mRNA transcription, JBC, 1990;265(3), 1516–1523, and Kilp A et al, Stimulation of hexose transport by metformin in L6 muscle cells in culture, Endocrinology, 1992;130(5), 2535–2544).

Uptake of 2DG was expressed as the percentage change compared with control. Values are presented as mean±SEM of sets of 4 wells per experiment. Differences between sets of wells were evaluated by Student's t test, probability values p<0.05 were considered to be significant. In the absence of added insulin, L6 cells incubated for 24 hours with the compound of formula I in which $R_1$ and $R_2$ are both H, showed a significant increase in 2DG uptake (from 100±2.1 in controls to 116.9±3.8, 123.9±4.3 and 134±7.3 at $10^{-8}$, $10^{-7}$ and $10^{-6}$ M respectively). In the presence of added insulin ($10^{-8}$ M), significant increases in 2DG uptake were observed following 24 hour incubation with the compound of formula I in which $R_1$ and $R_2$ are both methyl (sibutramine hydrochloride monohydrate) at $10^{-8}$ M (from 149.9±4.3 to165.3±2.6), the compound of formula I in which $R_1$ is methyl and $R_2$ is H at $10^{-7}$ M (from 147.3±3.0 to 160.7±4.5), and the compound of formula I in which $R_1$ and $R_2$ are both H, at $10^{-7}$ M and $10^{-6}$ M (from 149.1±3.9 to 161.8±3.3 and 165.2±3.6 respectively).

This study shows that in the presence or absence of added insulin, compounds of formula I increase glucose uptake in L6 muscle cells.

Study 2—In vivo ob/ob Mice

Studies were performed in obese ob/ob mice (Aston Strain) which are a model of severe insulin resistance and are also hyperglycaemic. The derivation and characteristics of this animal model have been previously described (Flatt P R, Bailey C J, Development of glucose intolerance and impaired plasma insulin response to glucose in obese hyperglycaemic (ob/ob) mice, Horm Metab Res 1981;13:556–560, and Bailey C J et al, Influence of genetic background and age on the expression of the obese hyperglycaemic syndrome in Aston ob/ob mice, Int J Obesity, 1982;6:11–21).

The ob/ob mice were individually housed in polypropylene cages at a temperature of 21±1° C. and 55% humidity. The mice had free access to a standard rat and mouse pelleted diet (Compound Rat and Mouse Diet, Special Diet Services, Witham, Essex) and tap water at all times. Animals were maintained on a reverse phase light-dark cycle. Lights were off between 09.00 h and 17.00 h in the acute experiment and between 10.00 h and 18.00 h in the chronic experiment. During this time the laboratory was illuminated by red lamps. Animals were acclimatised to these conditions for at least two weeks before experimentation.

All animals were given deionised water (at the start of the dark period) for 7 days. Body weight and food intake were measured daily. Blood samples were taken immediately before daily administration of vehicle (deionised water 10 ml/kg po) or compound of formula I in which $R_1$ and $R_2$ are both methyl (sibutramine hydrochloride monohydrate; 10 mg/kg po) on day 1 (baseline) and after 14 and 28 days of treatment (on day 15 and day 29 respectively). Blood samples were also taken 14 days following withdrawal of the sibutramine hydrochloride monohydrate (on day 43 of the study). Plasma glucose was determined by a glucose oxidase procedure (Analox GM7) and plasma insulin determined by radioimmunoassay (Amerlex, Amersham).

No significant changes in body weight or food intake were observed between vehicle and sibutramine hydrochloride monohydrate. Plasma glucose in sibutramine hydrochloride monohydrate-treated ob/ob fell after 14 and 28 days of treatment, with a significant difference from control at day 28 (P<0.01, Table 1). After 14 days of drug withdrawal, plasma glucose was unaffected in the vehicle dosed group but rose significantly in the sibutramine hydrochloride monohydrate treated group to control values. No significant changes in plasma insulin were observed though plasma insulin tended to fall in the sibutramine hydrochloride monohydrate treated group and increased on compound withdrawal.

Study 3—In vivo ob/ob Mice

Young ob/ob mice (Aston Strain) were randomised into 3 groups as follows: control, receiving placebo treatment (phosphate buffered saline 2.5 ml/kg/day po); sibutramine hydrochloride monohydrate-treated (5 mg/kg/day po); and pair-fed control, supplied with the same daily food intake as that consumed by the sibutramine hydrochloride monohydrate-treated group on the previous day. There was a 1 week run-in period followed by 6 weeks of treatment. Body weight and food intake were monitored every 1 to 2 days, and blood samples for plasma glucose and insulin were taken from the tail vein at weekly intervals in the non-fasted state at 11 a.m. An ip glucose tolerance test (D-glucose, 2 g/kg in 40% w/v solution in distilled water) and an insulin hypoglycaemia test (Actrapid, Novo-Nordisk, 2.5 u/kg ip) were conducted after 5 weeks of treatment. Food was withheld only for the duration of these tests (approx. 4 hours). The basal blood samples and the test procedures were undertaken 18 hours after the last treatment administration.

Treatment was stopped after 6 weeks, and the mice were monitored for the next 6 weeks. The pair-fed mice continued to be pair-fed with respect to the sibutramine hydrochloride monohydrate withdrawal group. A second insulin hypoglycaemia test was conducted 4 weeks after treatment was stopped. Plasma glucose was determined by an automated glucose oxidase procedure (Beckman) and plasma insulin determined by radioimmunnoassay (Amerlex, Amersham).

During sibutramine hydrochloride monohydrate treatment, significant reduction in body weight and plasma insulin compared to vehicle were observed. In an ip glucose tolerance test significant reductions in plasma insulin (P<0.05; see FIG. 1) and in plasma glucose (P<0.05; see FIG. 2) were observed with sibutramine hydrochloride monohydrate treatment compared to the vehicle treated group. Significant improvements in insulin hypoglycaemia (P<0.05; see FIG. 3; at 5 weeks) with sibutramine hydrochloride monohydrate treatment compared to the vehicle treated group were also observed. These results indicate that compounds of formula I, at a relatively low dose, are able to provide an improvement in insulin sensitivity because there is better glucose utilisation with less insulin. The pair-fed group showed a similar weight reduction to the sibutramine hydrochloride monohydrate treated group, but no improvement was observed in the oral glucose tolerance test. Therefore the pair-fed group do not show an improvement in insulin sensitivity.

During the sibutramine hydrochloride monohydrate withdrawal period, body weight and plasma insulin remained significantly lower than the vehicle treated group for almost all of the 6 week withdrawal period.

Figure 2:
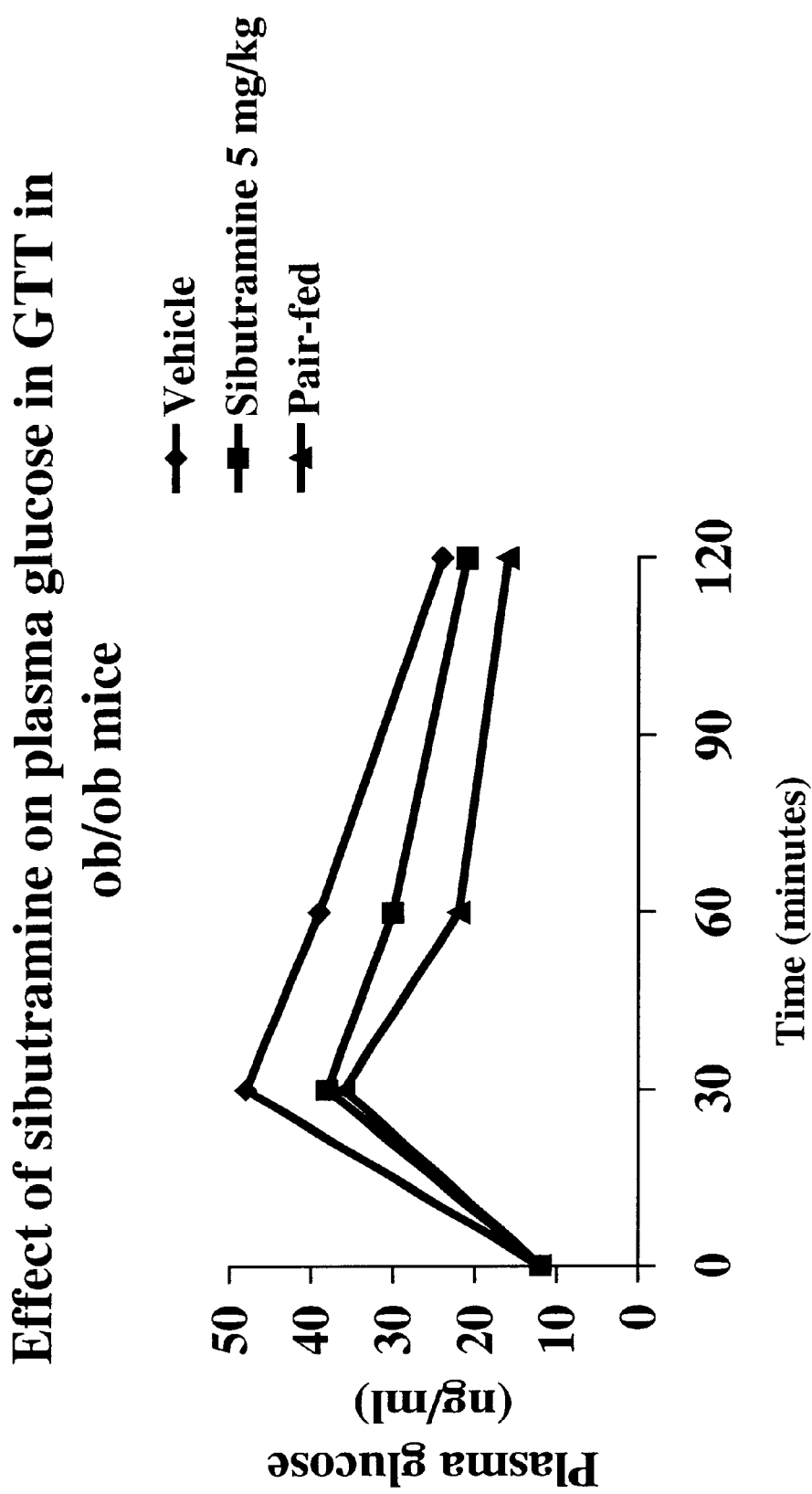
Figure 3:
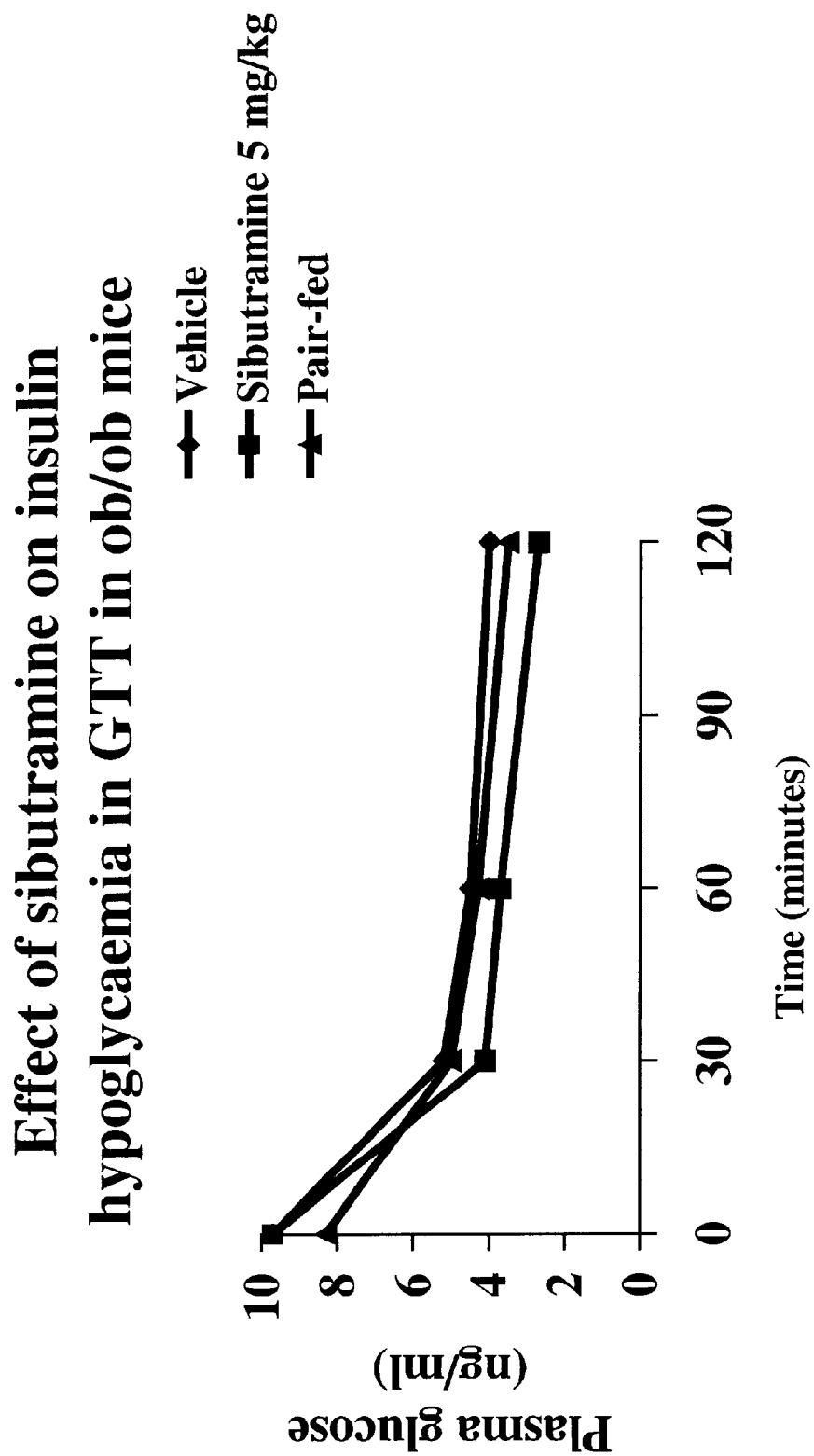

In Table 1 and FIGS. 1–3, "sibutramine" indicates "sibutramine hydrochloride monohydrate".

TABLE 1

Effect of chronic administration of the compound of formula I in which $R_1$ and $R_2$ are both methyl (10 mg/kg po) and its withdrawal on plasma glucose and plasma insulin in ob/ob mice.

| Treatment | Treatment Day of Study | Days | Vehicle (n) | Compound (n) | Plasma glucose (mmol/l) | | Plasma insulin (ng/ml) | |
|---|---|---|---|---|---|---|---|---|
| | | | | | Vehicle | Compound | Vehicle | Compound |
| Prior to treatment | 1 | 0 | 22 | 32 | 24.3 ± 0.6 | 24.3 ± 0.6 | 92.0 ± 4.5 | 92.0 ± 4.5 |
| Sibutramine | 15 | 14 | 22 | 32 | 21.7 ± 0.9 | 19.0 ± 0.6 | 49.7 ± 3.5 | 45.1 ± 2.6 |
| Sibutramine | 29 | 28 | 14 | 21 | 26.0 ± 1.4 | 15.8 ± 0.7** | 46.2 ± 4.5 | 35.1 ± 2.7 |
| Drug Withdrawal | 43 | 14 | 6 | 12 | 22.9 ± 1.7 | 23.6 ± 1.2 | 40.6 ± 8.6 | 77.1 ± 11.3 |

Values are back-transformed means ± SEM adjusted for differences between the treatment groups at baseline. Significant differences from the vehicle-treated control group are denoted by **$P < 0.01$. (n) is the number of animals involved.

The data from the three studies indicate that compounds of formula I can enhance both basal and insulin stimulated glucose uptake into the L6 muscle cells and that in the absence of changes in either body weight or food intake, the compound of formula I in which $R_1$ and $R_2$ are both methyl can reduce plasma glucose levels in ob/ob mice. These data taken together suggest an insulin sensitising action of compounds of formula I. The data also indicate the ability of compounds of formula I to decrease insulin resistance.

There are a several syndromes, such as acanthosis nigricans, leprechaunism, lipoatrophy and polycystic ovary syndrome, which exhibit insulin resistance as part of their profile. The above data suggest that a compound of formula I may have utility in alleviating the insulin resistance in humans having such conditions. Therefore the present invention further provides the use of a compound of formula I in the manufacture of a medicament for reducing insulin resistance in humans having acanthosis nigricans, leprechaunism, lipoatrophy or polycystic ovary syndrome or other conditions in which insulin resistance is present.

The present invention also provides a method of treatment for acanthosis nigricans, leprechaunism, lipoatrophy or polycystic ovary syndrome or other conditions in which insulin resistance is present, comprising administration of a compound of formula I to a patient in need thereof in conjunction with a pharmaceutically acceptable diluent or carrier.

NIDDM patients are often treated with oral insulin secretagogues, such as 1,1-dimethyl-2-(2-morpholinophenyl)guanidine fumarate (BTS67582) or sulfonylureas including tolbutamide, tolazamide, chlorpropamide, glibenclamide, glimepiride, glipizide and gliclazide, or with insulin sensitising agents including metformin, ciglitazone, troglitazone and pioglitazone. A further use of a compound of formula I is in the manufacture of a medicament, for combination therapy of NIDDM patients to improve their weight and diabetic control, comprising a compound of formula I and an oral insulin secretagogue or an insulin sensitising agent.

The present invention further provides a method of improving the weight and diabetic control of NIDDM patients comprising the administration of a compound of formula I in combination with an oral insulin secretagogue or an insulin sensitising agent in conjunction with a pharmaceutically acceptable diluent or carrier to a human in need thereof.

Preferably, the oral insulin secretagogue is 1,1-dimethyl-2-(2-morpholinophenyl)guanidine fumarate (BTS67582) or a sulphonylurea selected from tolbutamide, tolazamide, chlorpropamide, glibenclamide, glimepiride, glipizide and gliclazide. Preferably, the insulin sensitising agent is selected from metformin, ciglitazone, troglitazone and pioglitazone.

The compound of formula I and the oral insulin secretagogue or insulin sensitising agent may be administered either concomitantly or concurrently, for example in the form of separate dosage units to be used simultaneously, separately or sequentially. Accordingly, the present invention further provides a product containing a compound of formula I and an oral insulin secretagogue or insulin sensitising agent as a combined preparation for simultaneous, separate or sequential use for the improvement of weight and diabetic control in NIDDM patents. The ratio of the compound of formula I to the oral insulin secretagogue or insulin sensitising agent is such that the quantity of each active ingredient employed will be such as to provide a therapeutically effective level, but will not be larger than the quantity recommended as safe for administration.

The action of reducing insulin, resistance shown by compounds of formula I indicates that compounds of formula I may be useful in the manufacture of a medicament which can be used as an insulin sensitiser. Accordingly, the present invention further provides the use of a compound of formula I in the manufacture of a medicament which is an insulin sensitiser.

Some patients who are diagnosed as being Insulin Dependent Diabetics can also show a certain amount of insulin resistance. Therefore, there may be benefits in treating these patients with a compound of formula I in order to reduce their insulin resistance. This would mean that these patients would require a lower dosage of insulin in order to maintain similar or better control of their diabetes since the insulin dose would be associated with a greater blood glucose lowering efficacy. Such therapy would provide long-term benefits in terms of reducing the detrimental effects which can be caused by prolonged high-dosage of insulin treatment. Additionally, some NIDDM patients are also treated with insulin and have insulin resistance. Accordingly the present invention further provides a method for, and the use of a compound of formula I in the manufacture of the medicament for, reducing the amount of insulin required daily by a human having Insulin Dependent Diabetes Mellitus or NIDDM. The present invention also provides a method for, and the use of a compound of formula I in the manufacture of a medicament for, the prophylaxis of long-term detrimental effects caused by prolonged high dosage of insulin in humans having Insulin Dependent Diabetes Mellitus or NIDDM.

What is claimed is:

1. A pharmaceutical product for improvement of weight and diabetic control in NIDDM patients, which product comprises effective amounts of a compound of formula I

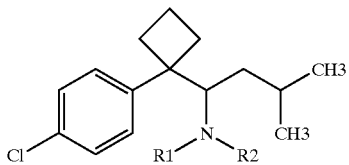

wherein $R_1$ and $R_2$ are independently H or methyl, or an enantiomer or pharmaceutically acceptable salt thereof, as a first active component, and an oral insulin secretagogue or insulin sensitizing agent as a second active component, in conjunction with at least one pharmaceutically acceptable diluent or carrier.

2. The product defined in claim 1, wherein the second active component is selected from the group of 1,1-dimethyl-2-(2-morpholinophenyl)guanidine fumarate (BTS67582) and a sulfonylurea selected from tolbutamide, tolazamide, chlorpropamide, glibenclamide, glimepiride, glipizide and gliclazide.

3. The product defined in claim 1, wherein the second active component is selected from the group of metformin, ciglitazone, troglitazone and pioglitazone.

4. The product defined in claim 1, wherein the first active component is N,N-dimethyl-1-[1-(4-chlorophenyl) cyclobutyl]-3-methylbutylamine hydrochloride.

5. The product defined in claim 1, wherein the first active component is N,N-dimethyl-1-[1-(4-chlorophenyl) cyclobutyl]-3-methylbutylamine hydrochloride in the form of its monohydrate.

6. The product defined in claim 1, which is adapted for simultaneous, separate or sequential administration of the first and the second active component.

7. The product defined in claim 6, wherein the second active component is selected from the group of 1,1-dimethyl-2-(2-morpholinophenyl)guanidine fumarate (BTS67582) and a sulfonylurea selected from tolbutamide, tolazamide, chlorpropamide, glibenclamide, glimepiride, glipizide and gliclazide.

8. The product defined in claim 6, wherein the second active component is selected from the group of metformin, ciglitazone, troglitazone and pioglitazone.

9. A method of improving the weight and diabetic control of NIDDM patients which comprises administering an effective amount of the product defined in claim 1 to a human in need thereof.

10. The method of claim 9, wherein the second active component is selected from the group of 1,1-dimethyl-2-(2-morpholinophenyl)guanidine fumarate (BTS67582) and a sulfonylurea selected from tolbutamide, tolazamide, chlorpropamide, glibenclamide, glimepiride, glipizide and gliclazide.

11. The method of claim 9, wherein the second active component is selected from the group of metformin, ciglitazone, troglitazone and pioglitazone.

12. The method of claim 9, wherein the first active component is N,N-dimethyl-1-[1-(4-chlorophenyl) cyclobutyl]-3-methylbutylamine hydrochloride.

13. The method of claim 9, wherein the first active component is N,N-dimethyl-1-[1-(4-chlorophenyl) cyclobutyl]-3-methylbutylamine hydrochloride in the form of its monohydrate.

14. The method of claim 9, wherein the first and the second active component are administered simultaneously, separately or sequentially.

* * * * *